US011386606B2

United States Patent
Mory et al.

(10) Patent No.: US 11,386,606 B2
(45) Date of Patent: Jul. 12, 2022

(54) SYSTEMS AND METHODS FOR GENERATING ENHANCED DIAGNOSTIC IMAGES FROM 3D MEDICAL IMAGE

(71) Applicant: KONINKLIJKE PHILIPS N.V., Eindhoven (NL)

(72) Inventors: Benoit Jean-Dominique Bertrand Maurice Mory, Medford, MA (US); Emmanuel Moce Serge Attia, Paris (FR); Jean-Michel Rouet, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 91 days.

(21) Appl. No.: 17/047,003

(22) PCT Filed: Apr. 2, 2019

(86) PCT No.: PCT/EP2019/058225
§ 371 (c)(1),
(2) Date: Oct. 12, 2020

(87) PCT Pub. No.: WO2019/197203
PCT Pub. Date: Oct. 17, 2019

(65) Prior Publication Data
US 2022/0005258 A1    Jan. 6, 2022

(30) Foreign Application Priority Data

Apr. 11, 2018  (EP) .................................. 18290032

(51) Int. Cl.
*G06T 15/08*     (2011.01)
*G06T 7/50*      (2017.01)
(Continued)

(52) U.S. Cl.
CPC .............. *G06T 15/08* (2013.01); *A61B 8/463* (2013.01); *A61B 8/466* (2013.01); *A61B 8/523* (2013.01);
(Continued)

(58) Field of Classification Search
None
See application file for complete search history.

(56) References Cited

U.S. PATENT DOCUMENTS 6,530,885 B1    3/2003  Entrekin et al.
2006/0197780 A1*  9/2006  Watkins .................. G06T 19/00
                                                    345/620
(Continued)

FOREIGN PATENT DOCUMENTS

WO    2008127927 A1    10/2008

OTHER PUBLICATIONS

PCT/EP2019/058225 ISR & WO.

*Primary Examiner* — Yanna Wu

(57) ABSTRACT

The present disclosure describes a medical imaging and/or visualization system and method that provide a user interface enabling a user to visualize (e.g., via a volume rendering) a three dimensional (3D) dataset, manipulate the rendered volume to select a slice plane, and generate a diagnostic image at the selected slice plane, which is enhanced by depth colorized background information. The depth colorization of the background image is produced by blending, preferably based on the depth of structures in the volume, two differently colorized volume renderings, and then fusing the background image with a foreground diagnostic image to produce the enhanced diagnostic image.

19 Claims, 12 Drawing Sheets

(51) Int. Cl.
    *G16H 30/40*    (2018.01)
    *A61B 8/00*     (2006.01)
    *A61B 8/08*     (2006.01)
    *G01S 7/52*     (2006.01)
    *G01S 15/89*    (2006.01)
    *G06T 5/50*     (2006.01)

(52) U.S. Cl.
    CPC ...... *G01S 7/52053* (2013.01); *G01S 15/8925* (2013.01); *G01S 15/8993* (2013.01); *G06T 5/50* (2013.01); *G06T 7/50* (2017.01); *G16H 30/40* (2018.01); *G06T 2200/04* (2013.01); *G06T 2207/10024* (2013.01); *G06T 2207/10136* (2013.01); *G06T 2207/20092* (2013.01); *G06T 2207/20132* (2013.01); *G06T 2207/20216* (2013.01); *G06T 2207/20221* (2013.01); *G06T 2210/41* (2013.01)

(56) References Cited

U.S. PATENT DOCUMENTS

| | | | |
|---|---|---|---|
| 2014/0073925 A1 | 3/2014 | Kho et al. | |
| 2015/0065877 A1* | 3/2015 | Orderud | A61B 8/466 600/438 |
| 2016/0125640 A1* | 5/2016 | Lee | A61B 8/463 600/443 |

* cited by examiner

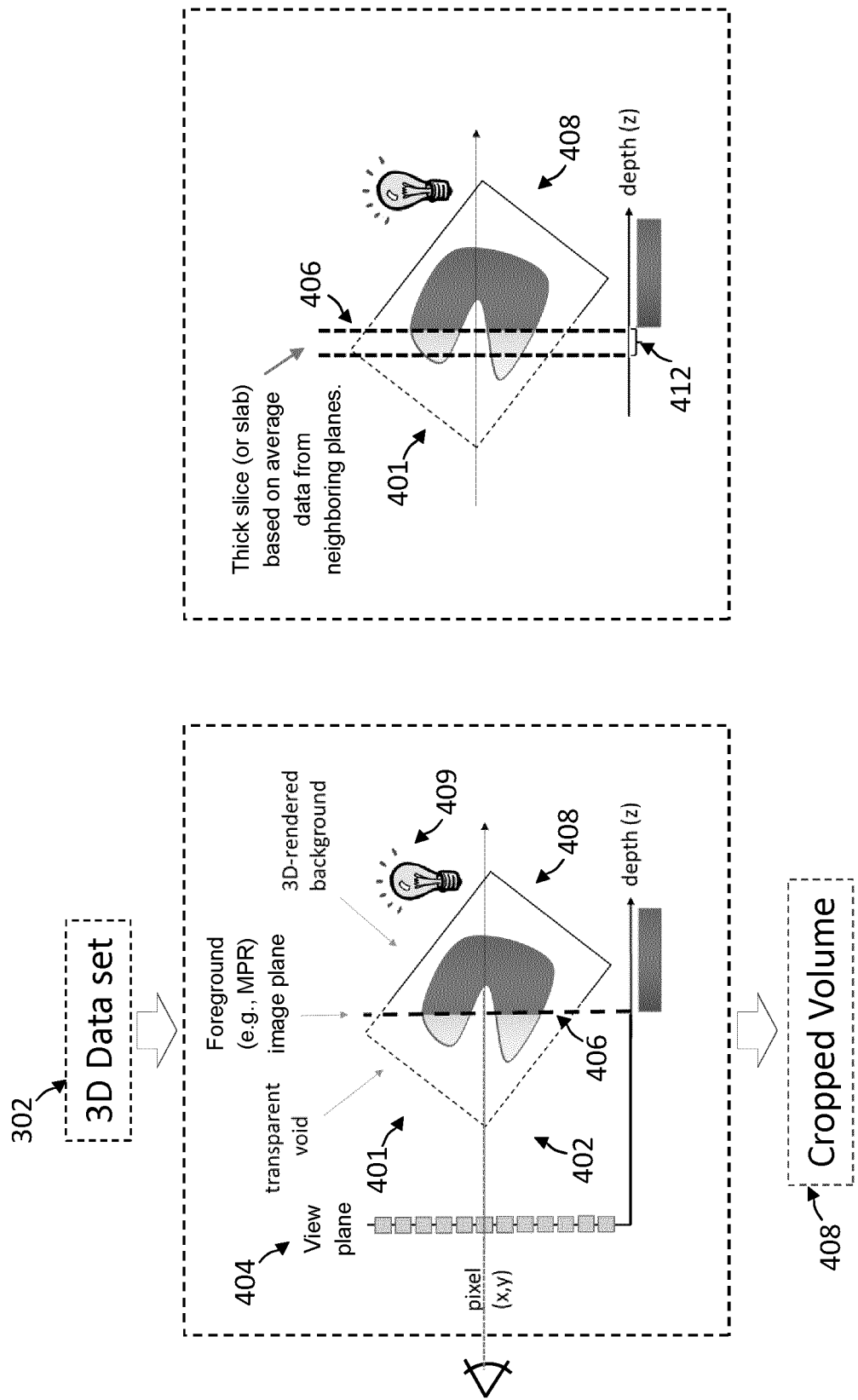

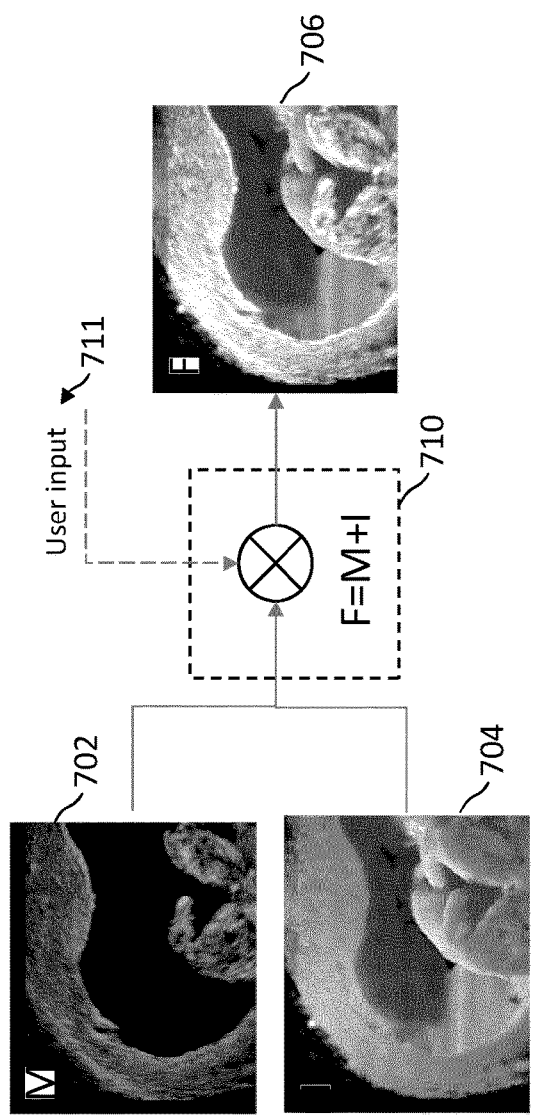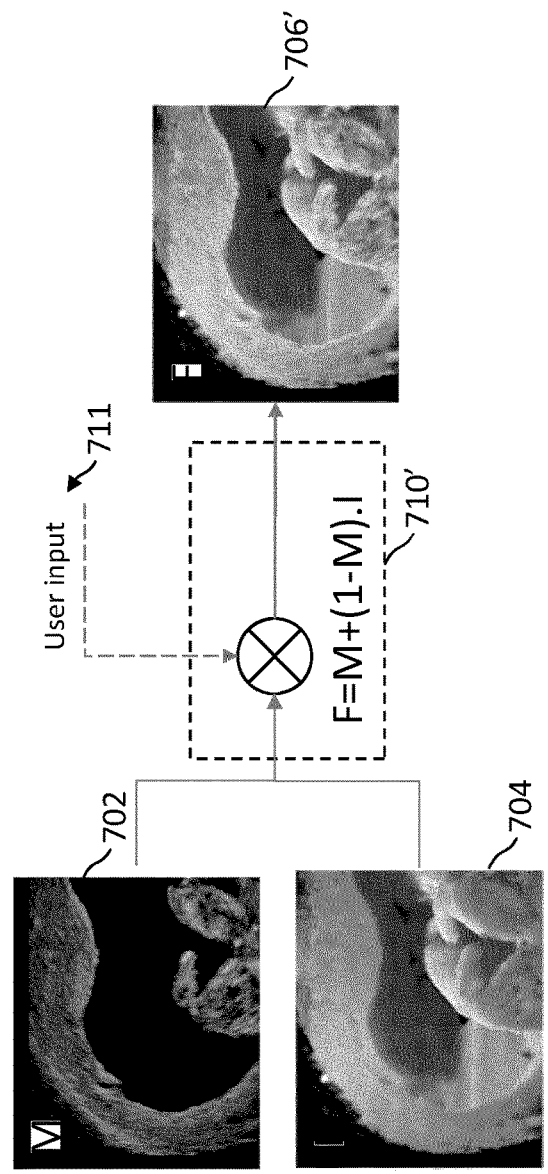
FIG. 7A
FIG. 7B

US 11,386,606 B2

SYSTEMS AND METHODS FOR GENERATING ENHANCED DIAGNOSTIC IMAGES FROM 3D MEDICAL IMAGE

CROSS-REFERENCE TO PRIOR APPLICATIONS

This application is the U.S. National Phase application under 35 U.S.C. § 371 of International Application No. PCT/EP2019/058225, filed on Apr. 2, 2019, which claims the benefit of European Patent Application No. filed on Apr. 11, 2018. These applications are hereby incorporated by reference herein.

FIELD OF THE INVENTION

The present disclosure relates generally to medical imaging systems, such as ultrasound imaging and/or analysis systems, and methods for acquisition and/or display of 3D medical imaging data.

BACKGROUND OF THE INVENTION

Displaying 3D volumes on a 2D screen typically involves one of two main families of visualization techniques: slicing, such as via Multi-Planar Reformatting (MPR) to display a 2D image (e.g., a slice or slab), and volume rendering, such as via splatting, Maximum Intensity Projection, or other known surface or volume rendering technique.

With respect to volume rendering, previously developed techniques required the 3D Volume to be first converted into a set of discrete and quantized surfaces (e.g. Marching Cubes algorithm). Another more recently developed technique allows one to create a 3D-like image directly from a 3D object (i.e., a 3D matrix of numbers). This technique utilizes an optical physics model of how the eye/retina sees the visual world, where the model describes a method by which a ray cast line (corresponding to a single pixel of the image plane) would intersect the volume in a manner dependent upon the viewer's location with respect to the 3D object being visualized. The value assigned to the pixel thus involves a compositing operation, which would integrate the interpolated samples along the ray cast line. Such a method is now used for almost all 3D medical imaging applications.

While volume rendering may enhance the visualization of context (e.g., surrounding anatomical structure) for the benefit of the clinician or patient, diagnostic determination is typically obtained from 2D slice images as these images are better capable of providing the relevant and more accurate diagnostic information. Although certain techniques for combining the information from 2D and 3D images have been developed (e.g., side-by-side display or simple overlays), designers and manufacturers of 3D ultrasound imaging systems continue to seek improvements thereto.

SUMMARY OF THE INVENTION

In accordance with some examples, a medical imaging data visualization system may include an input device connected to a source of 3D medical imaging data, an output device operable to connect to a display (e.g., for providing images to a user), and memory and a processor connected to the input and output devices. The processor may be programmed to receive, from the source of 3D medical imaging data, a 3D dataset representative of a volume of imaged biological tissue. The processor may be further programmed to position the 3D dataset relative to a viewing plane, generate a 2D image at a slice plane through the volume, crop the volume at the slice plane, and generate first and second color volume renderings of the cropped volume from a same viewing perspective. The first and second color volume renderings are associated with respective first and second different color maps. The processor may be further programmed to blend the first and second color volume renderings to produce a background image and to combine the 2D image, which provides foreground information, with the background image to produce a composite medical image. In some embodiments, the medical imaging data visualization system described herein is incorporated in an ultrasound scanner. For example, the input device may include any suitable hardware components (e.g., input/output connectors, data bus and/or other circuitry) for connecting the processor to an output of a signal processor of an ultrasound scanner which generates the 3D medical imaging data, e.g., responsive to ultrasound echoes detected by a probe of the scanner. The output device may include any suitable hardware components (e.g., input/output connectors, data bus and/or other circuitry) for connecting the processor to a display device (e.g., a main display or touch-screen display of an ultrasound scanner). In some embodiments, the processor of an example system that generates the volume renderings and blends foreground and background image data may be a processor (e.g., a CPU, GPU, or another) of an ultrasound scanner. In other embodiments, the processor may be part of a separate computing system, which does not acquire the image data but displays previously acquired data. In some embodiments, the visualization system may be implemented in a visualization workstation, which is connected (via the input device) to a storage device (e.g., a PACS server) that stores pre-acquired 3D medical imaging data.

The processor of a system according to the present disclosure may be configured to produce and store a number of intermediate images prior to generating the composite medical image. For example, the processor may be configured to produce a first single-channel (i.e. grayscale) image and couple the first single-channel image to memory, and to further produce a second single-channel (i.e. grayscale) image and couple the second single-channel image to memory. The first and second single-channel images may comprise a grayscale depth map image and a grayscale luminance image, respective. The depth map image may be generated by estimating, for each pixel in an image, a depth (or distance from the viewing plane) to the first encountered non-zero value in the 3D dataset at the given pixel. The estimated depth may be encoded and stored as the grayscale value of the given pixel. The luminance image may be generated by applying a physical model of how light reflects off the bodily structures represented by the 3D dataset and encoding and storing this information (e.g., the estimated reflected light at each given pixel) as the grayscale value of each pixel. The luminance image output is dependent on the viewing perspective and the location of the virtual light source utilized by the model, both of which may be defaulted to a certain position at the start of the process and/or configurable by the user during the visualization process. The processor then maps the pixel values from two single-channel (grayscale) images to a multi-channel image using a pre-stored 2D color map (e.g., a depth vs. luminance color map). For example, the corresponding color value for each pair of grayscale values at a given pixel in the depth map and luminance images is encoded as the new, and now multi-channel, pixel value for that pixel. This multi-channel image represents a first color volume rendering of the 3D dataset and is stored in memory until accessed by the blending algorithm.

Additionally, the processor generates a second color volume rendering using a different colorization scheme (i.e. different color map) than the color rendering produced from the grayscale depth and luminance images. The second color rendering may be produced by applying the same or similar physical model of how light intersects with and reflects off the bodily structures represented by the 3D dataset, but in this case encoding the results from the model directly into a multi-channel (e.g., RGB or other color-encoding scheme) output for each pixel. The second color volume rendering is also stored in memory until accessed by the blending algorithm.

The blending process involves the combining of the pixel data from the first and second color volume renderings. In one embodiment, the processor is programmed to blend the color pixel values of each pair of corresponding pixels of the first and second color volume renderings as a function of the estimated distance associated with the given pair of pixels. In this embodiment, the processor receives as input the pixel data from the first and second color volume renderings and the pixel data from the grayscale depth map image. The processor applies a blending function, for example a convex blending function to the input data and outputs a new multi-channel value for each pixel. The blended multi-channel image data, sometimes referred to herein as background image, is stored in memory until retrieved for fusing with the foreground image data. In some embodiments, prior to blending, the depth values are normalized (e.g., mapped to unit-less values in a normalized range of 0-1). In some embodiments, the processor automatically defines the minimum ($d_{min}$) and maximum ($d_{max}$) values corresponding to the minimum (Z=0) and maximum (Z=1) values of the normalized range. The normalization may be dynamic in that the range is updated whenever the volume is repositioned or re-cropped.

The processor is configured to produce a combined or composite medical image by fusing the blended multi-channel image data (or background image data) with the 2D slice image data (or foreground image data). The foreground image can be produced using any known technique for generating a 2D diagnostic image (e.g., a grayscale B-mode image). For example, the fusion algorithm may receive as input a grayscale B-mode image (although, non-grayscale images, such as colorflow or color power angio images, may also be used) and the blended multi-channel image, and combine the image data by summing the image data. In some embodiments, a scaling factor may be applied to one or both of the input values during the summation. For example, a scaling factor may be applied during the summation, which may produce improved results particularly in conditions of front lighting, e.g., with the light source located in front of the slice plane. The output of the fusion process is a combined colored image that includes diagnostic image information at the foreground (e.g., at the slice plane) enhanced with contextual rendered information as background (e.g., at any pixel location which would otherwise have been out of the image plane in the diagnostic image). In some embodiments, the processor may be configured to receive user input to adjust the amount of foreground and background information presented in the composite image. For example, the fusion algorithm may be adaptable responsive to user input which user input may adjust the scaling factor(s) applied by the fusion algorithm.

A method of visualizing 3D medical image data may include displaying a volume rendering of a 3D dataset representative of a volume of imaged biological tissue, cropping the volume responsive to an indication of a selected slice plane and generating a foreground image comprising a 2D slice image at the selected slice plane. The method may further include generating, using a first color map, a first color volume rendering of the cropped volume and generating, using a second color map, a second color volume rendering of the cropped volume. The method may further include blending the first and second color volume renderings to produce a background image, wherein the blending is based at least in part on estimated depth of structures in the cropped volume, and combining the foreground image and the background image to produce a composite medical image.

Additionally, any of the techniques for rendering 3D datasets described herein may be embodied in processor-executable instructions stored on non-transitory computer-readable medium, which when executed cause a processor of a medical visualization and/or imaging system to be programmed to perform the processes embodied in the non-transitory computer-readable medium.

BRIEF DESCRIPTION OF THE DRAWINGS

FIGS. 4A and 4B illustrate concepts of volume rendering and cropping within a virtual 3D space in accordance with the principles of the present disclosure.

FIGS. 7A and 7B are functional block diagram of a fusion block of a processor in accordance with some embodiments of the present disclosure.

DETAILED DESCRIPTION OF EMBODIMENTS

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Displaying images of 3D volumes (or 3D datasets) on a 2D screen involves either slicing (e.g., generating one or more MPR views at a specified slice plane through the volume) or displaying a rendering of the volume (also referred to as volume rendering). 2D slice image(s) extracted from a 3D volume can show small details and subtle variations of tissue texture, which may be difficult to provide in a 3D rendered image as they are generally produced from the image data associated only with the slice plane or by averaging image data associated with a small number neighboring planes. Slice images therefore do not provide depth information. Conventional volume renderings on the other hand provide depth information and can therefore enable the visualization and understanding of the 3D shape of an anatomical structure, but may not be sufficiently detailed or accurate for diagnostic measurements. In accordance with the principles of the present disclosure, a system and method for a 3D visualization mode that shows structures at different depths on a single image, including a 3D rendered background and a 2D diagnostic foreground image, are described. In some examples, the techniques described herein may involve enriching a photo-realistic rendering with artificial depth colorization and MPR fusion to provide anatomical context to diagnostic images.

Figure 1:
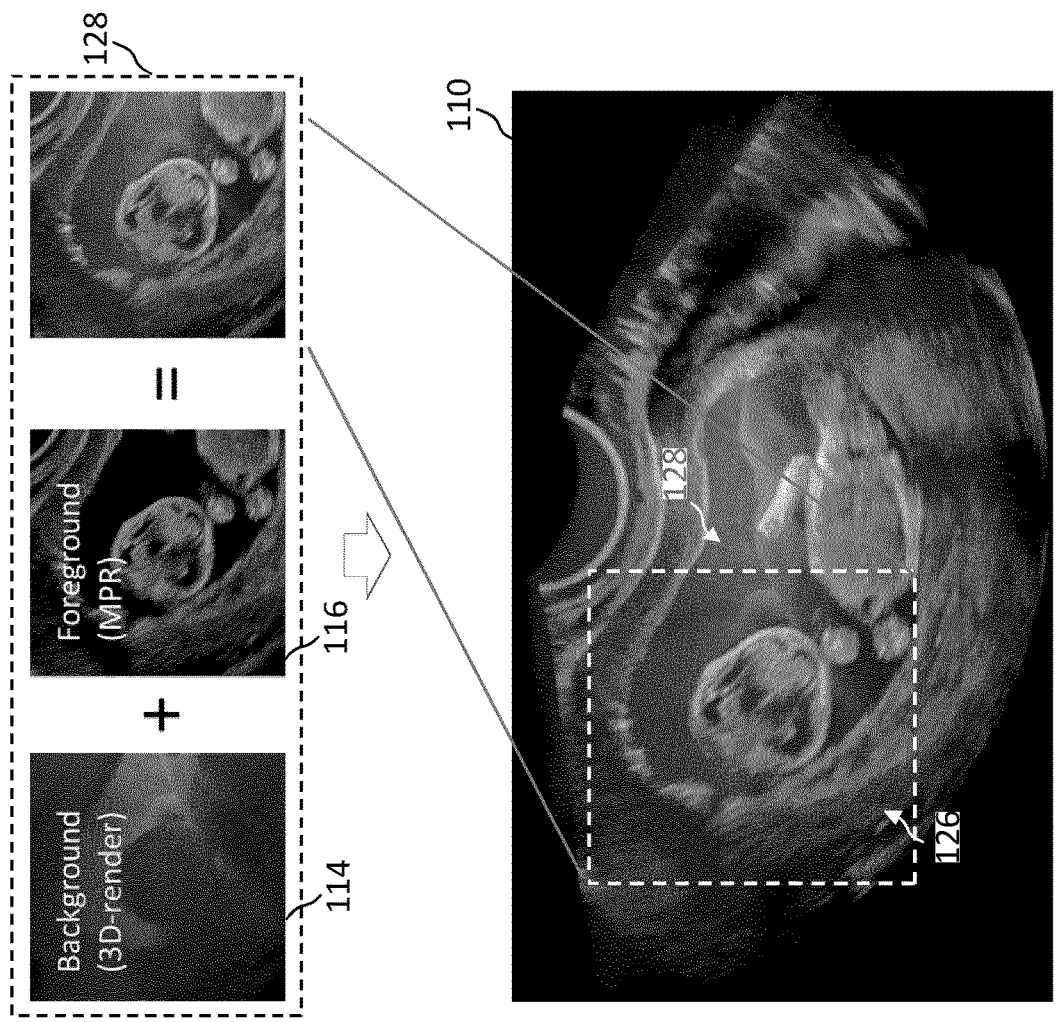
FIG. 1 is an illustration of a composite medical image produced in accordance with principles of the present disclosure.

In accordance with principles of the present invention, a medical visualization and/or imaging system (e.g., an ultrasound system) is configured to produce a diagnostic image (e.g., a planar reconstruction (MPR) image) with depth-colorized photo-realistic context, which may also be referred to herein as enhanced MPR image. FIG. 1 shows an example of a composite ultrasound image 110 produced from a 3D dataset of ultrasound imaging data in accordance with the principles of the present disclosure. While examples herein are described with reference to ultrasound imaging and ultrasound-based image data, it will be understood that the principles of the present disclosure are equally applicable to other imaging modalities (e.g., magnetic resonance (MR), computed tomography (CT), positron emission tomography (PET), etc.). That is, enhanced medical images that include foreground diagnostic information with background rendered data may be generated from any 3D medical image data sets obtained using virtually any medical imaging modality. The image 110 in the example in FIG. 1 includes a foreground or diagnostic image portion 126 and a background image portion 124. The foreground image portion 126 may include only or predominantly diagnostic image data 116, while the background image portion 128 may include only or mostly background (e.g., volume-rendered) image data 114. The foreground (116) and background (114) images may be generated and fused (as shown in block 128) into the final combined image 110 in accordance with the principles of the present disclosure. In the illustrated example, the foreground image is an MPR image 116 generated in accordance with known techniques for producing a 2D MPR slice image from a 3D ultrasound dataset (although, other techniques may be used and on different source data in other examples). The background image 114 is a volume rendering of the 3D ultrasound dataset (cropped at the selected MPR plane of the image 116) and produced in accordance with the techniques described herein. The combined image 110 may thus provide an enhanced diagnostic image by combining diagnostic image information with depth-colorized photo-realistic context.

Figure 2:
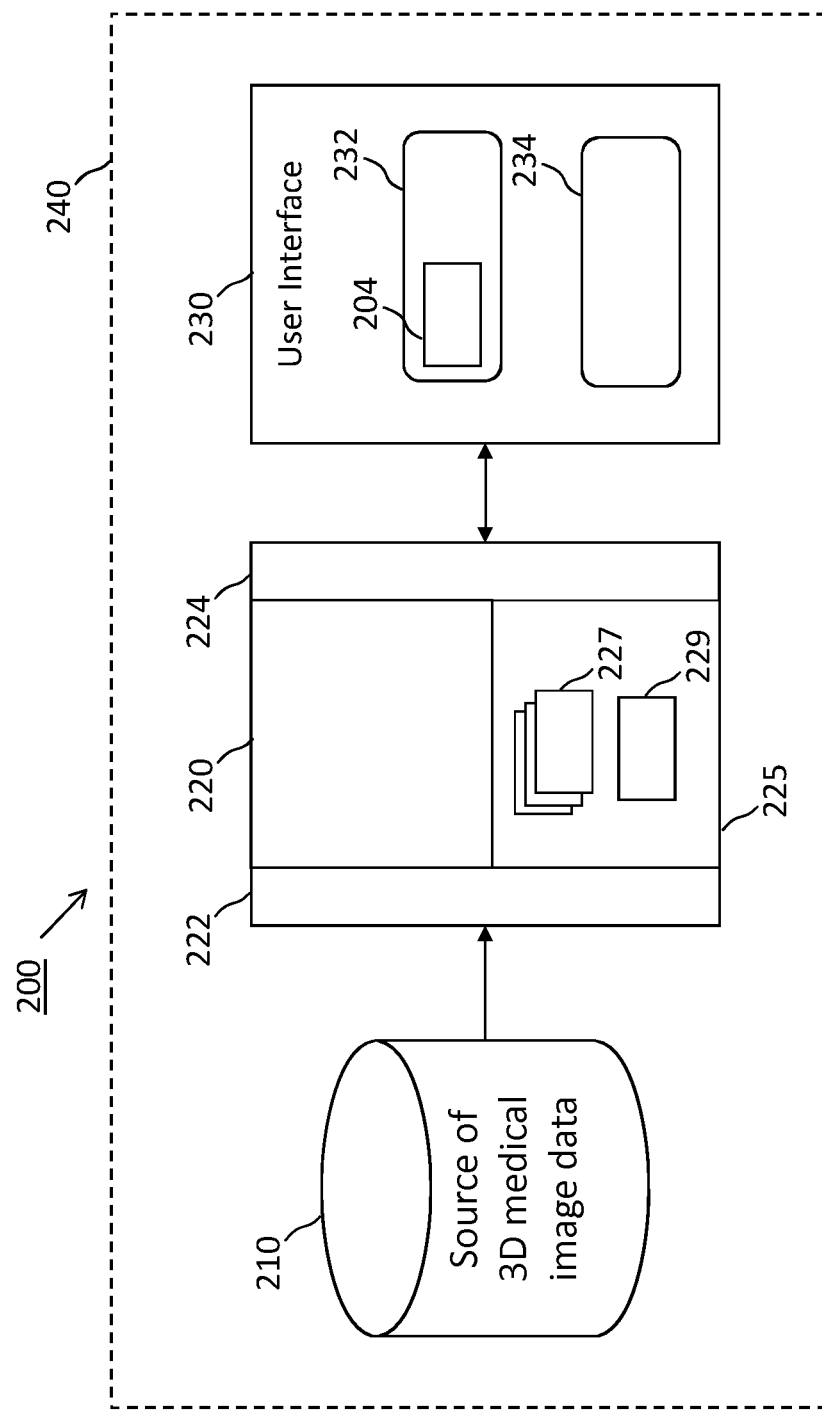
FIG. 2 is a block diagram of a medical image data visualization system in accordance with the principles of the present disclosure.

FIG. 2 shows a system 200 in accordance with principles of the present invention. System 200 includes a data processor 220 configured to produce a combined or composite medical image 204 (e.g., ultrasound image 110 of FIG. 1). System 200 includes a processor 220, a memory 225, an input device 222 configured to couple the processor 220 and memory 225 to a source of 3D medical image data 210, and an output device 224 configured to couple the processor 220 and memory 225 to a user interface 230 (e.g., a display) and/or a storage device for outputting the composite medical image (e.g., for presentation to a user or for storage). In some embodiments, the input and output devices may include any type of suitable computer hardware interface (e.g., parallel, serial, USB or any other type of port or connector coupled to a data bus of the system) for connecting the processor 220 to the source of medical image data and to the display, respectively. In some embodiments, the input and output devices may be implemented using any suitable input/output device, e.g., for connecting to a peripheral device (e.g., external memory, a display, etc.). In some embodiments, the input device may be or include at least one databus connected to processor 220 and further connected or connectable to a source of medical image data (e.g., a storage device comprising non-volatile memory and/or imaging components of a medical scanner).

In some embodiments, the source of 3D medical image data 210 may be an ultrasound scanner or a medical scanner of a different modality (e.g., MRI, CT, PET etc.). In some such embodiments, some or all of the components of system 200 may be incorporated into a medical imaging system 240, for example in an ultrasound imaging system as and described further with reference to FIG. 9. In other embodiments, the source of 3D medical image data 210 may be a medical image data storage device, e.g., a storage device of a picture archiving and communication system (PACS) of a hospital or other medical facility.

The memory 225 may be configured to store one or more intermediate images 227 produced by processor 220 and used in generating the final composite image. The memory 225 may also store executable instructions and/or parameters 229 (e.g., color maps, scaling factors, etc.) for volume rendering and/or blending image data produced by processor 220. The user interface 230 may include a display device 232 operable to display the image 204 and a user-input device 234 configured to receive user input(s) e.g., for manipulation of the 3D image data and/or image 204. The components and the arrangement thereof shown in FIG. 2 are merely illustrative, and other variations, including eliminating components, combining components, rearranging components, and substituting components are all contemplated.

Figure 3:
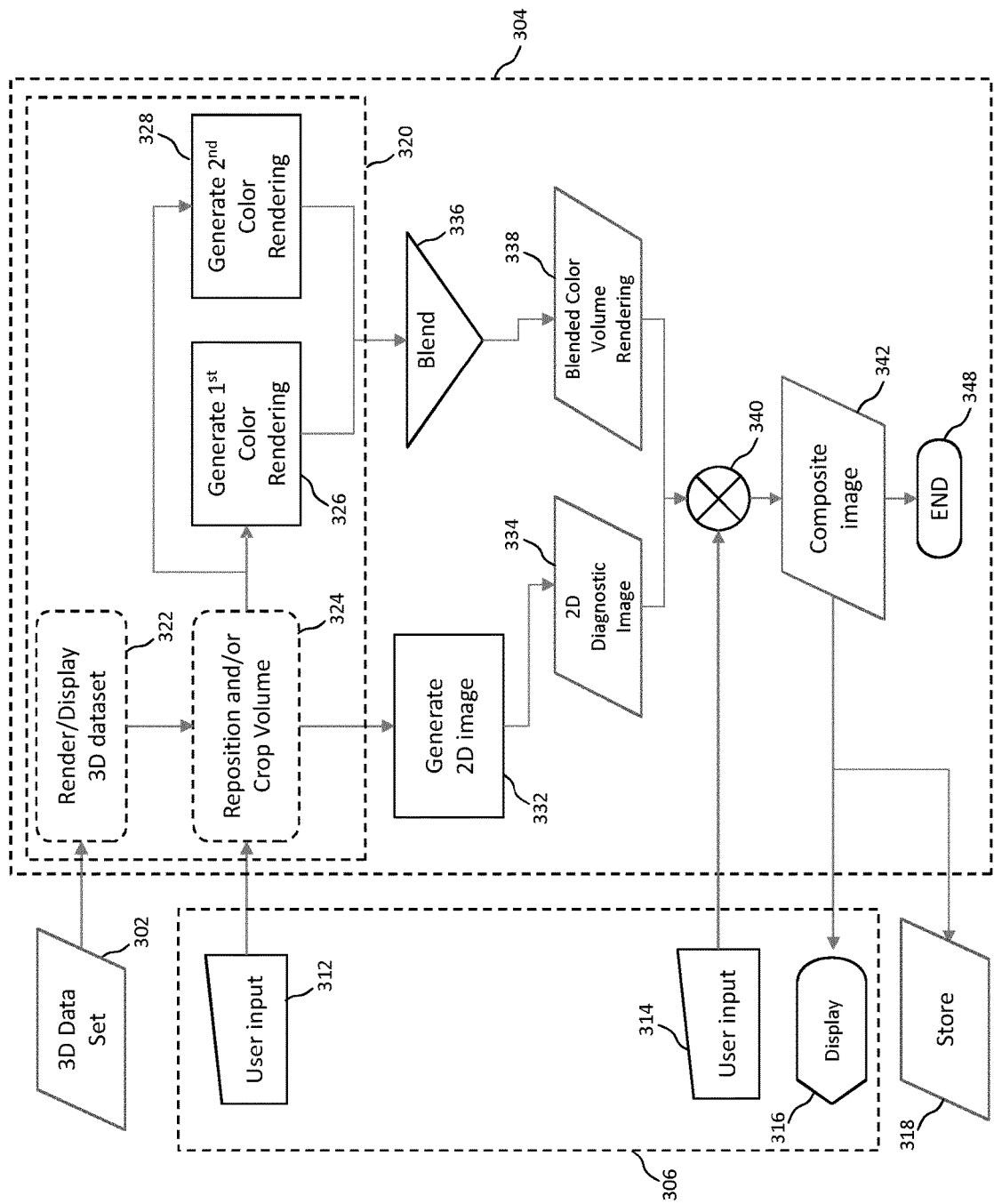
FIG. 3 is a function block diagram of a processor in accordance with some embodiments of the present disclosure.

Referring now also to FIGS. 3-5, components and operation of systems in accordance with the principles of the present invention are further described. FIG. 3 shows a functional block diagram of a processor 304. The processor 304 may be used to implement processor 220 in FIG. 2. The processor 304 may be programmed to receive, from a source of 3D medical imaging data 210, a 3D dataset 302 representative of a volume of imaged biological tissue. The processor 304 may implement a volume-rendering engine 320. The volume-rendering engine 320 may be programmed to generate a volume rendering of a 3D dataset (e.g., a 3D matrix of pixel data) in accordance with any known technique (e.g., volumetric ray-casting, splatting, shear warp volume rendering, etc.). The processor 304 may thus be able to generate a volume rendering of the 3D dataset 302 and cause the rendering to be displayed on display, as shown in block 322. In providing the volume rendering for display, the processor 304 may position the 3D dataset or volume 401 within a virtual 3D space 402 and thus relative to a viewing plane 405 (see FIG. 4A). The volume 401 is initially positioned at a default distance (or depth z) and orientation in relation to the viewing plane 404.

As shown in block 324, the processor 304 may receive user input 312 for manipulating the volume 401 within the virtual 3D space, e.g., to reposition the volume 401 (e.g., adjust the distance and/or orientation of the volume) with respect to the viewing plane 405. As is known, volume rendering algorithms may utilize a physical model of how light intersects and/or reflects from structures in the volume (represented by non-zero data within the 3D dataset) and output this information as either single-channel or multi-channel pixel data for producing a grayscale or color image, respectively. In addition to manipulating the volume 401 to reposition it, the processor 304 may be further configured to receive user input 312 for cropping the volume at a selected slice plane 406. Upon receipt of a selected slice plane, the processor 304 may in effect remove the voxels in front of the slice plane (i.e. between the slice plane 406 and viewing plane 404) and produce a volume rendering of the cropped volume 408 including pixel data representative only of the voxels at and behind the slice plane. The rendering may be updated following any further manipulation of the volume and/or rendering parameters (e.g., light source position, intensity, etc.) by the user.

Once an indication of a slice plane 406 has been received, the processor 304 is programmed to produce a 2D image at the slice plane, as shown in block 332. This may be done using any known technique for generating 2D medical images such as multiplanar reformatting or reconstruction. The 2D image 334 (e.g., MPR image) is considered a diagnostic image in that it is generally configured to convey a sufficient level of detail of medical imaging information as may be needed by a clinician to make diagnostic decisions. In contrast, the volume rendering produced at block 322 would not typically be considered a diagnostic image as it would not typically provide sufficient level of detail for diagnostic purposes. In some embodiments, and as shown in FIG. 4B, the processor 304 may be configured to produce thick slice 2D images, for example by averaging the image data from one or more image planes 412 adjacent to the indicated slice plane 406. The 2D image is stored in memory, as shown in block 334, until accessed later by the processor 304 for fusion with the background image.

In addition to the 2D diagnostic image, the processor 304 is further programmed to produce a number of additional images (e.g., images 510, 512, 514, and 518 in FIGS. 5A and 5B) of the cropped volume 408 from the same viewing direction as defined by the relative position of the volume 401 to the viewing plane 404. As will be described further with reference to FIGS. 5A and 5B, the processor 304 is configured to produce a first color volume rendering of the cropped volume (as shown in block 326) using a first colorization scheme, and a second color volume rendering of the cropped volume (as shown in block 328) using a second different colorization scheme. That is, the first and second color volume renderings may each be associated with respective first and second different color maps. The processor 304 is further programmed to blend the first and second color volume renderings, as shown in block 336, to produce a blended color volume rendering 338, which will be used as the background image.

As shown in block 340, the processor 304 is configured to combine the 2D image 334, which provides the foreground information, with the blended color volume rendering 338, which provides the background information to produce a composite medical image 342. The processor 304 may be configured to receive user input, as shown in block 314, to adjust one or more parameters of the blending process. For example, the processor may be configured to provide a user control via the user interface 306 for receiving user input to control the amount of foreground and background information included in the combined image 342. The combined image 342 may be output by processor 304 for storage (e.g., block 318) or display (e.g., block 316), after which the process may terminate (at block 348).

Figure 5A:
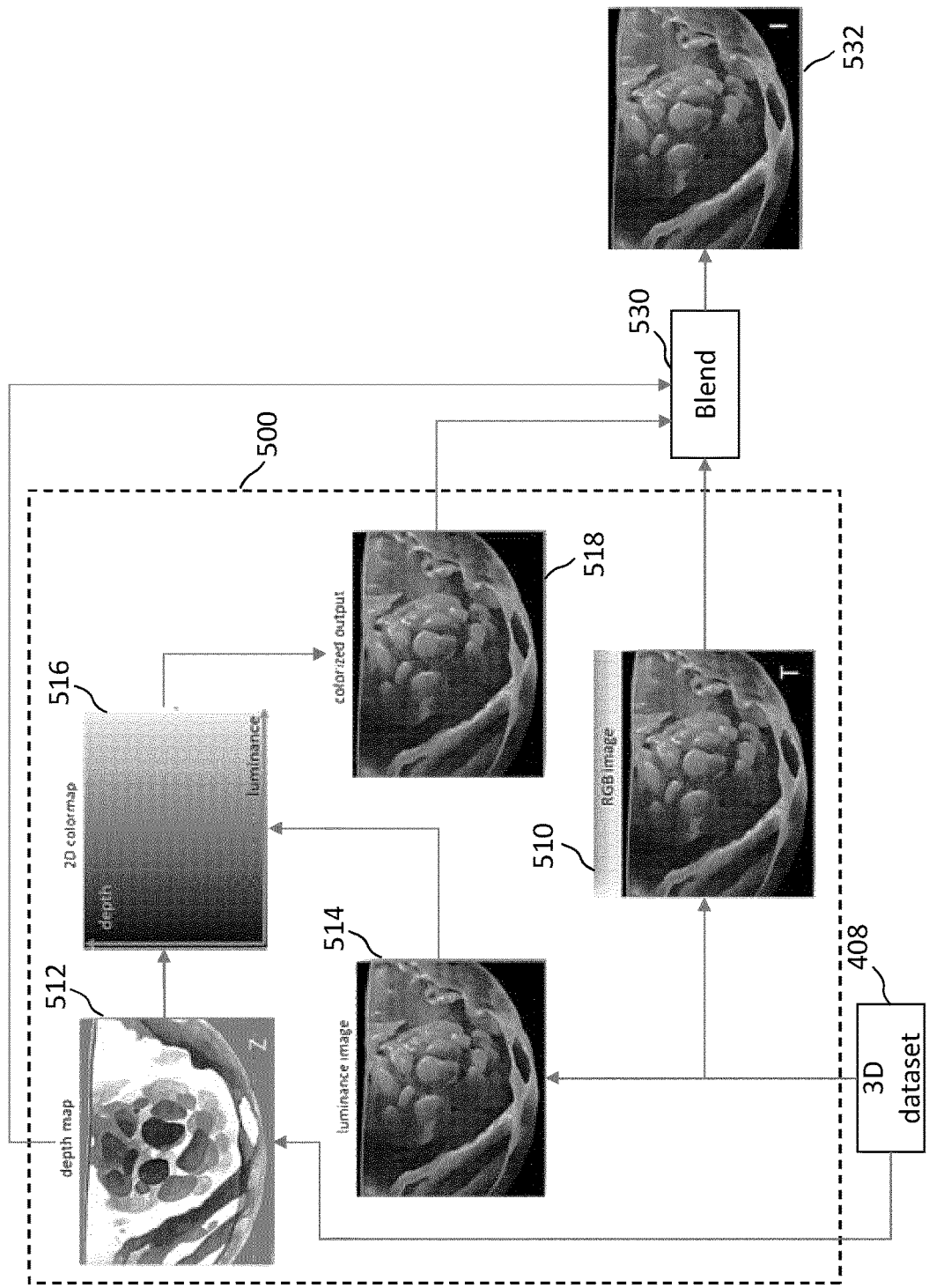
FIGS. 5A and 5B are functional block diagrams of processors for producing colorized volume renderings in accordance with some embodiments of the present disclosure.
Figure 5B:
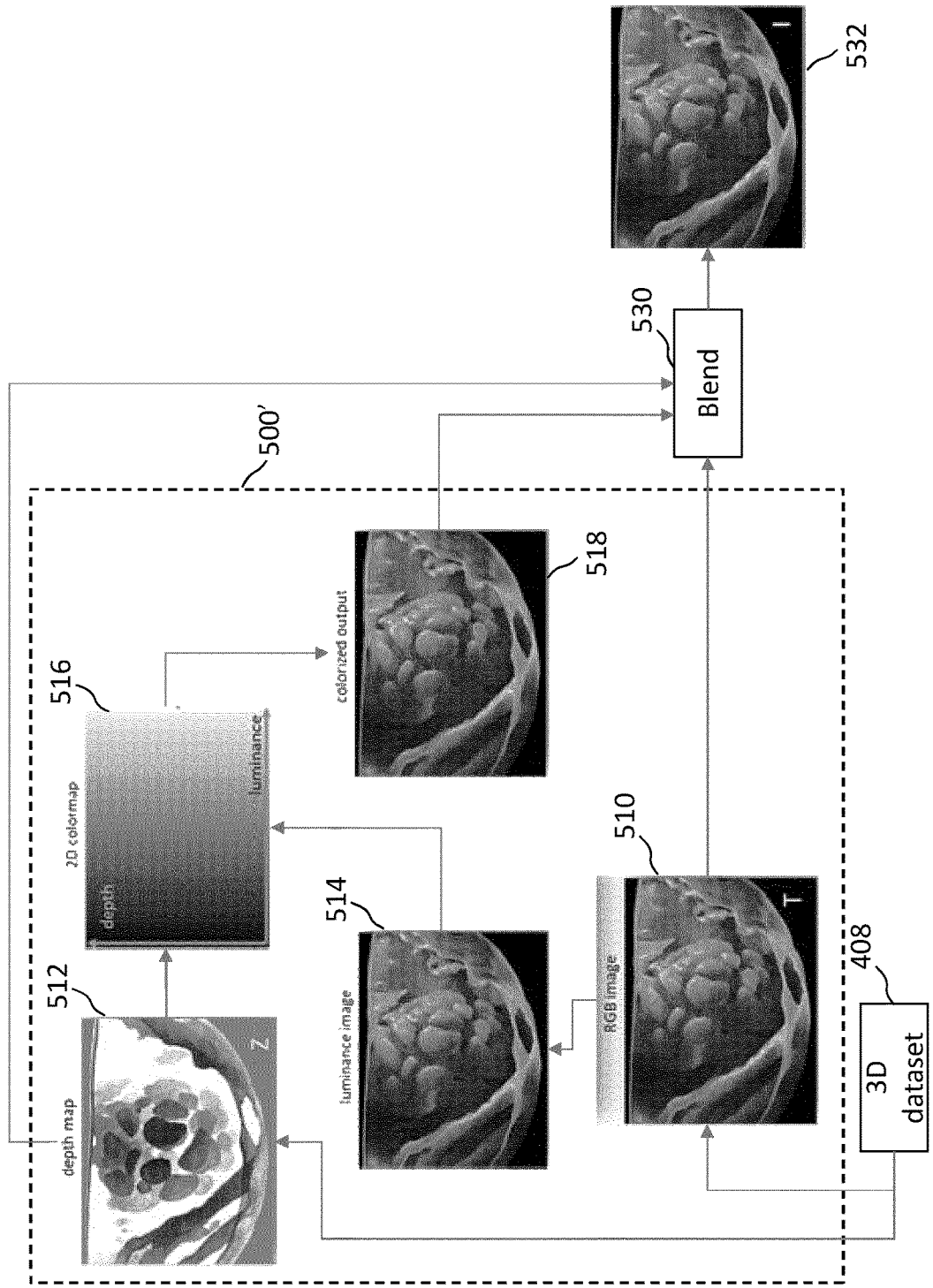

FIGS. 5A and 5B show processing blocks and image data generated by a processor (e.g., a volume renderer) according to the present disclosure. The processor 500, 500' may implement any known volume-rendering algorithm to produce volume renderings of the input dataset 408. The processor 500, 500' may be used to implement, in part, the processor 320 of FIG. 3. As shown in FIG. 5A, processor 500 receives, as input, a 3D dataset of medical image data (e.g., a cropped volume output from block 324 in FIG. 3), and outputs a pair of color volume renderings 510 and 518, which are then blended at block 530 to produce the blended or enhanced background image 532. The intermediate images 510, 512, 514, and 518 encode different information of the same input data set. For example, the color renderings 510 and 518 are volume renderings of the same view of the imaged volume but colorized using two different color maps.

The color image 518 is produced by colorizing a volume rendering of the input dataset 408 according to a first colorization scheme (e.g., 2D color map 516). To produce color image 518, the volume-rendering engine first generates a luminance image 514, which may be a grayscale volume rendering of the 3D dataset. This grayscale volume rendering is stored as a single-channel image 514. The grayscale rendering is then colorized based on the depth of the structures represented therein. This step adds depth cues to the rendering 514. To colorize the rendering 514, another grayscale image is output by the rendering engine—a grayscale depth map image 512, which encodes and stores the estimated depths of the structures in the image in a single-channel image. That is, the depth map image 512 may be generated by estimating, for each pixel in an image, a depth z (or distance from the viewing plane) to the first encountered anatomical structure (or non-zero value in the 3D dataset) along a ray passing through the given pixel. The estimated depth is then encoded and stored as the grayscale value of the given pixel, with darker pixels indicating structures closer to the viewing plane and conversely, lighter pixels indicating structures farther away from the viewing plane.

As described, the luminance image 514 may be generated by applying a physical model of how light intersects and/or reflects off the bodily structures represented by the 3D dataset and encoding and storing this information (e.g., the estimated reflected light at each given pixel) as the grayscale value of each pixel. The luminance image may be produced by any suitable volume rendering technique capable of outputting a grayscale rendering of a volumetric dataset. As noted, the luminance image 514 is dependent on the viewing perspective and the location of the virtual light source (e.g., 409 in FIG. 4A) utilized by the model, both of which may default to a certain preset at the start of the process and/or be configurable by the user during the initial visualization/rendering of the 3D dataset. For example, the use of backlighting (i.e. positioning the light source behind the slice plane or even behind the structures in the imaged volume, may be well suited to producing good depth colorization as it may result in a darkened background (e.g., near black) that ensures a good contrast with a foreground overlay containing bright (e.g., near white) structures. The processor 500 then maps the pixel values from two single-channel (grayscale) images 512, 514 to a multi-channel image 518 using a pre-stored 2D color map 516 (e.g., a depth vs. luminance color map). For example, using the depth vs. luminance color map 516 shown in FIG. 5A, each pair of pixel values from the images 512, 514 correspond to a color value, which is encoded as the new multi-channel value for that pixel in the image 518. In this manner, the grayscale luminance image 514 may be colorized using the 2D color map 516 to produce a color volume rendering 518 according to a first colorization scheme.

As further shown in FIG. 5A, the processor 500 also outputs a volume rendering 510 of the input data set 408, encoded using a different color map. The color image 510 may be colorized using a colorization scheme (e.g., an RGB color map) that is different from the color map applied to produce image 518. The image 510 may be generated by the volume-rendering engine using the same or similar rendering algorithm as used to produce the luminance image but in this case encoding the output in color rather than in grayscale. In some embodiments, a different color map may be applied as the first color scheme depending on the specific imaging application (e.g., cardiac, maternal-fetal or other obstetric imaging, etc.). Alternatively, as shown in FIG. 5B, the processor 510' may implement a volume rendering algorithm to first output the color rendering 510 based on the input data set 408. The color rendering (image 510) is stored for later use by the blending block 530. A single-channel (e.g., the R, G, or B channel, if using RGB color values) of the color image 510, or some combination of the values two or more of the multi-channel data, is encoded in a single-channel output as the luminance image 514. The processor 500' also produces a depth map image 512 as previously described, and the two grayscale images 512 and 514 are similarly mapped using a 2D color map 516 to the other color rendering (image 518). The two color volume renderings 510 and 518 may be coupled to memory, along with the depth map image 512, and used as inputs to the blending block 530.

Figure 6A:
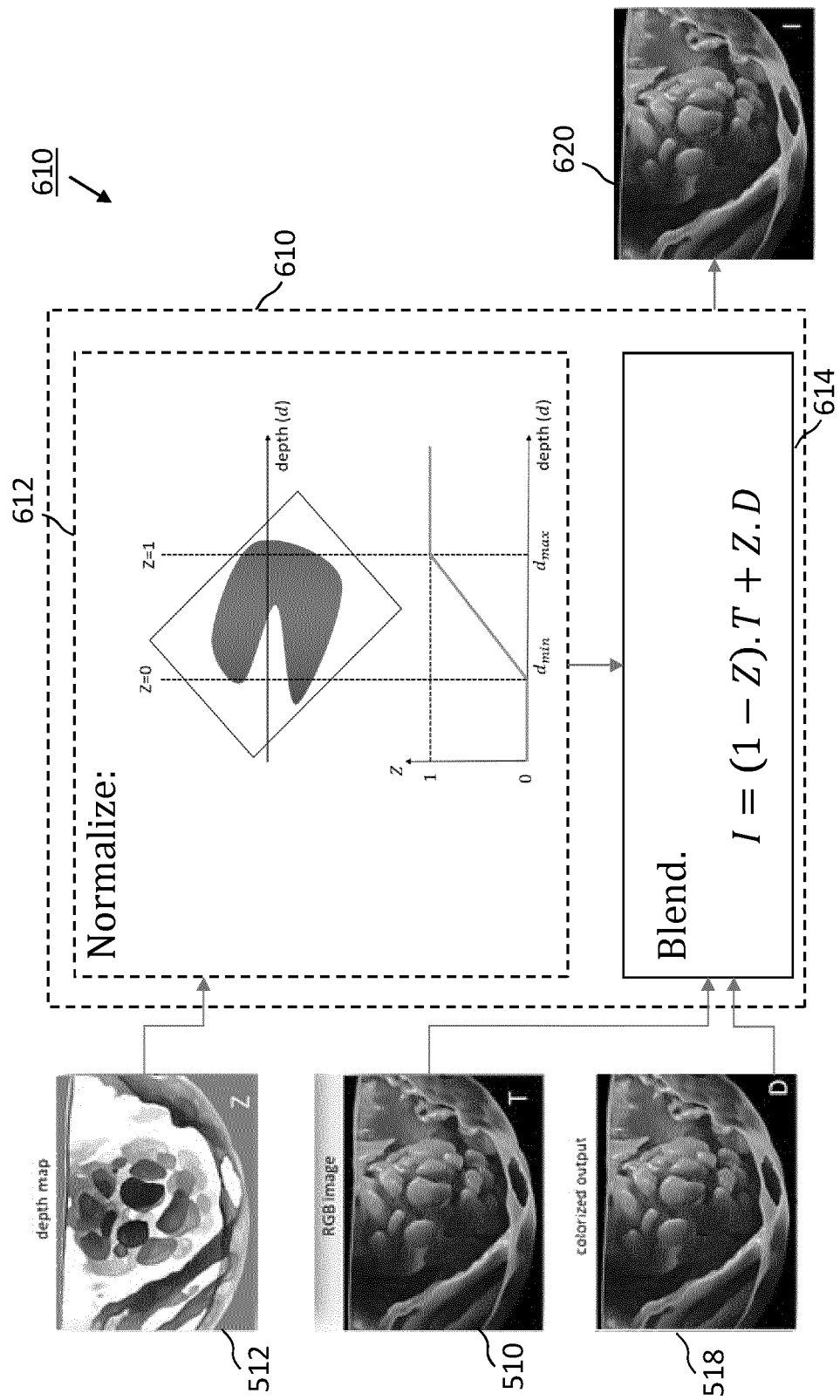
FIG. 6A is a functional diagram of a blending block of a processor in accordance with some embodiments of the present disclosure.

FIG. 6A shows a functional block diagram of components of a processor 600 according to the present disclosure, particularly blending block 610. Blending block 610 may be used to implement blocks 336 or 530 of FIGS. 3 and 5A-5B, respectively. The blending block 610 receives a first and second multi-channel images (e.g., color volume renderings 518 and 510) as inputs and provides, as output, a blended color image 620, which combines the pixel data from the first and second color volume renderings. The blended color image data is computed based on a blending algorithm, e.g., as shown in block 614. In one embodiment, the blending algorithm is defined as a function of the depth. As such, blending block 610 may also receive, as input, the estimated depth of the anatomical structures rendered in the images 518, 510 (e.g., the depth map image 512 produced by the volume-rendering engine). In one preferred embodiment, the processor 600 normalizes the depth values (e.g., by mapping them to a normalized range of 0-1), as shown in block 612. This may be achieved, for example, by applying a scaling function (e.g., a saturated affine function), as shown in block 612.

The blending block 610 may apply a convex blending algorithm to combine the color data of the two input color images (e.g., images 510 and 518). For example, the image data may be combined according to the function $I = (1-Z) \cdot T + Z \cdot D$, where T is the color image 510 output natively from the volume rendering engine, D is the color image 518 colorized produced by colorizing the luminance only imaged based the depth information, and Z is the normalized depth value for the corresponding pixel. By applying a convex combination using $(1-Z)$ and $Z$ as blending factors, the hue of near-field structures ($Z \approx 0$) may be better preserved, gradually becoming more artificial in the far-field ($Z \approx 1$), which can improve the color contrast of foreground structures while providing enhanced depth cues to physically-based rendered images.

As further illustrated, the processor 600 may normalize, in block 612, the estimated depth values (z) encoded in the depth map image 512 as depth values (Z) in the range of $Z \in [0,1]$. For example, a saturated affine function may be defined in block 612, by which any point in the 3D space for which the volume renderer has estimated a depth below $d_{min}$ is assigned $Z=0$ and thus the corresponding RGB values will remain untransformed, while any point that has been estimated to be at a distance beyond $d_{max}$ will be assigned $Z=1$, which corresponds to a maximally transformed hue (e.g., blue). Within the range $d_{min}-d_{max}$, hue is gradually (e.g., linearly) altered according to depth. In some embodiments, the values of $d_{max}$ and $d_{min}$ may be user-defined (e.g., depending on the specific imaging application (e.g., the type of tissue or organ being imaged) or user preference).

Figure 6B:
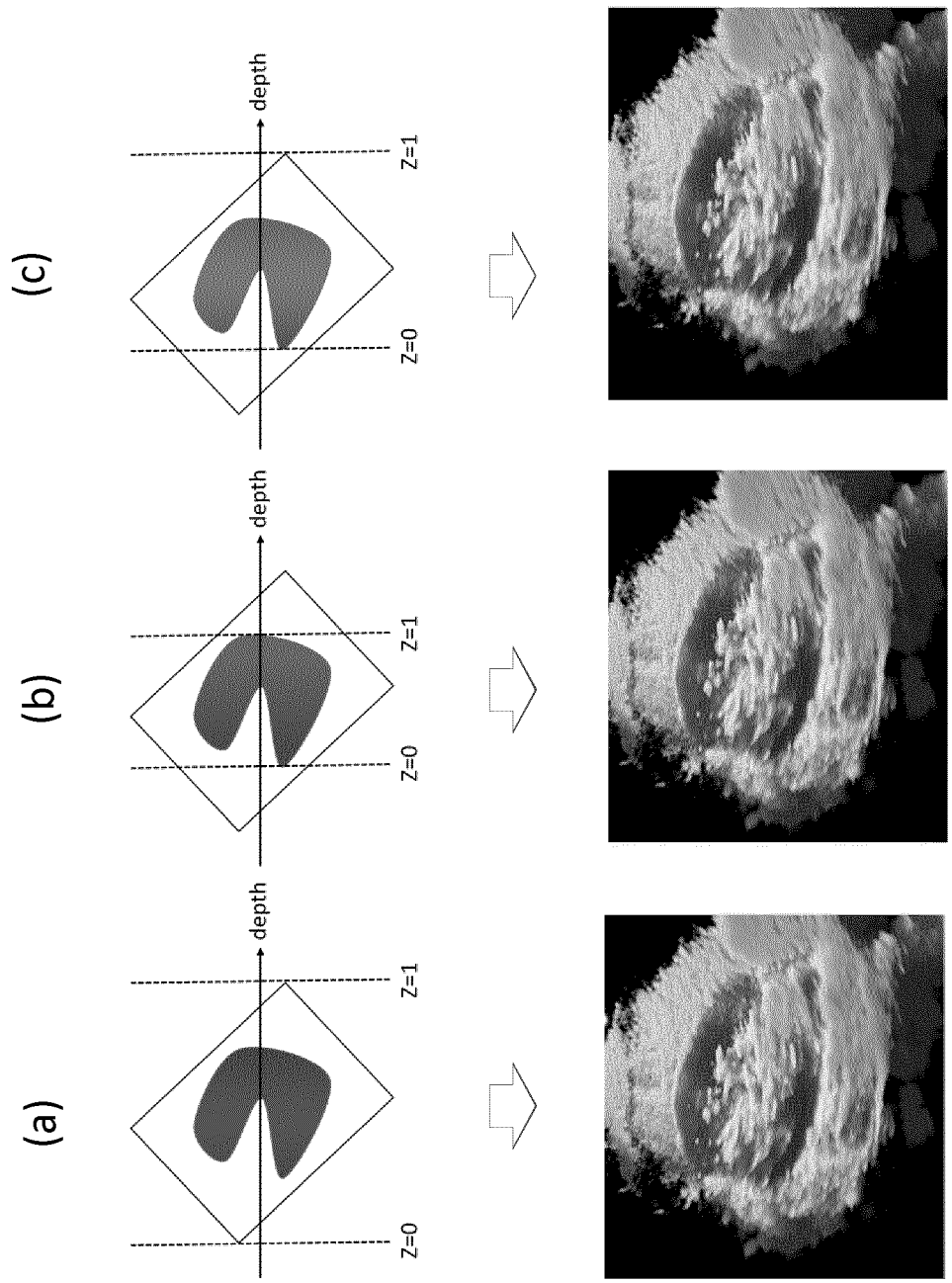
FIG. 6B illustrates concepts of geometry-based, content-based, or hybrid definition of a blending function in accordance with principles of the present disclosure.

In one preferred embodiment, the processor 600 may automatically define the scalar-valued function that maps the estimated depth to the range $Z \in [0,1]$, as shown in block 612, and more specifically the $d_{min}$ and $d_{max}$ values to be mapped to 0 and 1, respectively. Because a change of viewpoint can significantly affect the observed range of depth in the rendered image, the depth range should preferably be adapted to the position of the camera. The depth range may be automatically defined for any given viewpoint as follows. Generally, the depth range (i.e., $d_{min}$ and $d_{max}$) may be defined based on geometry or based on content. For example, as shown in FIG. 6B, panel (a), a geometry-based method relies only on the 3D geometrical configuration, i.e. the camera viewpoint and volume orientation relative to that viewpoint. As illustrated in (a), basic geometric considerations can provide minimum and maximum depths of the enclosing cuboid, regardless of the actual data found in that region. FIG. 6B, panel (b), illustrates a content-based approach. A content-based method may interrogate the input dataset or the depth map to calculate distance statistics on non-zero data points, providing what the effective depth range is for a given dataset and viewpoint. Statistics can be as simple as min-max operations, or use averaging over a region of the output image. The estimated range may depend not only on the values of the volumetric acquisition, but also on a "transfer function". Transfer function here refers to a transformation of the input dataset in order to make low-intensity structures within the dataset transparent so that such "transparent" voxels in the 3D space would not contribute to a content-based estimation of a depth range.

Each of the two techniques (geometry-based or content-based) has advantages and limitations. For example, adapting depth estimation to the actual data tends to be less stable to 3D rotation and image noise that may induce abrupt color changes. Also, opaque but invisible voxels that are occluded can still influence the estimation of the background location, for unintuitive effects on colors. Estimations based only on geometry are faster (no data to interrogate) and potentially more stable. But in general, especially when portions of the volume are empty, they tend to provide too broad a depth range, resulting in insufficient color contrast between structures at different depths. For instance, (a) illustrates that 3D rotations can lead to corner cases where front plane reference are located quite far from any content.

In some examples, a hybrid strategy, as shown in FIG. 6B, panel (c)), may be utilized for the automatic definition of the depth range. A content-based estimation may be better suited, in the present context, to locate the foreground depth, while geometry can define a more stable background reference. A hybrid estimation technique for depth range may thus involve defining $d_{min}$ as the minimal or average first hit, e.g., calculated with depth map statistics, and defining $d_{max}$ as the distance of the farthest corner of the enclosing cuboid. Using a content-based estimation for the front plane may guarantee a fundamental property of the colorization process, that is, that the front color would be preserved for any orientation, even in the presence of a cut plane that crops the volume and locates an MPR overlay. It will, of course be appreciated, that while a hybrid technique for the automatic definition of the $d_{min}$ and $d_{max}$ may be preferred and used in some examples, other embodies may utilize a different technique such as a geometry-based or content-based technique.

FIGS. 7A and 7B show a function block diagram of examples of a fusion block 710, 710' of a processor (e.g., processor 304) according to the present disclosure. The fusion block 710 or 710' may be used to implement block 340 in FIG. 3. As previously discussed, the processor combines the foreground and background images 702, 704, e.g., by summing the corresponding pixel values at each pixel location in the image, to produce a final composite image 706, 706'. In some embodiments, the fusion of the two images may involve a simple pixel-wise summation, as shown in FIG. 7A. For example, if M is the scalar-valued (i.e. single-channel) image produced for example by multi-planar reformatting at the crop plane, and I is the blended color (i.e. multi-channel) volume rendering (e.g., image 620) output from the blending block 610 following depth colorization, the combined or fused image F may be produced by simply summing the corresponding pixel of the two input images. In some embodiments, the pixel values of the scalar image are combined individually with each channel (e.g., R, G, and B) values for the corresponding pixels of the color image 704 to produce the output color image 706.

Figure 8:
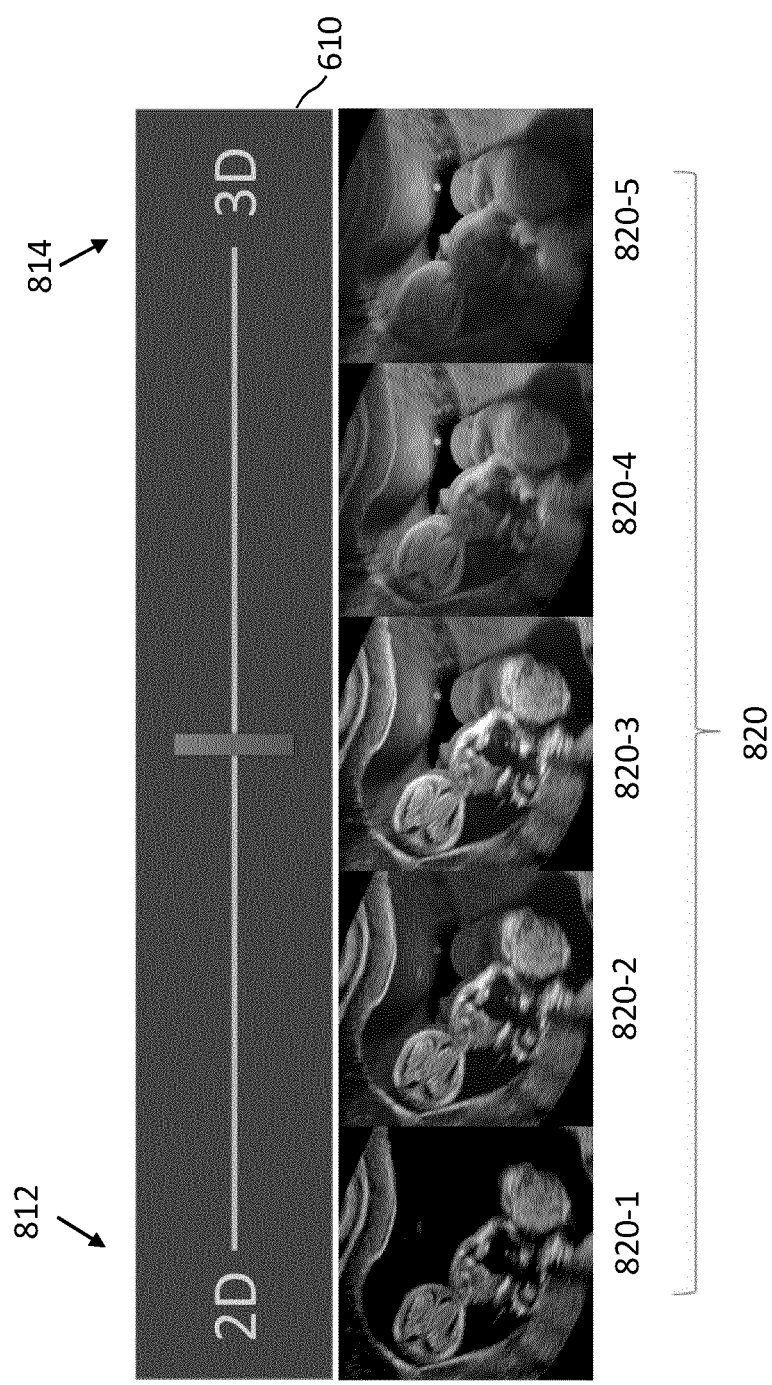
FIG. 8 is an illustration of an example user control for controlling a fusion operation of a processor in accordance with some embodiments of the present disclosure.

In some embodiments, the processor (e.g., processor 304) may be configured to receive user input 711 for adjusting the amount of background and foreground information in the final combined medical image 706. In such embodiments, the processor may be programmed to provide a user control (e.g., a soft control presented on a touch screen interface or other) to allow the user to indicate the amount of desired foreground and background information in the composite image. FIG. 8 illustrates an example optional user control 810 (e.g., a slider) which may be provided via the user interface when visualizing medical image data in an enhanced diagnostic mode. The user control 910 may allow the user to provide an indication of a desired higher amount of foreground information (e.g., by sliding the slider towards the left 812) or a desired lower amount of background information (e.g., by sliding the slider towards the right 814). The displayed composite image 820 may dynamically update (as shown by images 820-1 through 820-5) as the user adjusts the control 810 to provide an immediate feedback to the user as to the controlled blend of foreground and background information. The processor (e.g., processor 304) may adjust the scaling factor of the fusion algorithm (e.g., in block 340) responsive to the received indication of desired amount of foreground or background content. Other types of user controls (e.g., hard controls such as buttons, sliders, etc. or soft controls) may be used. For example, the system may be configured to receive the adjustment via operation of a trackball of an ultrasound scanner or analysis workstation, or the user may provide the adjustment via text input, or other. The indicated desired amount of foreground/background information may be coupled to the fusion block 710, which may apply a scaling factor (linear or non-linear) to the values of the input images when performing the summation.

Returning back to FIGS. 7A and 7B, the pixel-wise summation in the example of FIG. 7A may be well suited for backlit scenes where the rendered background is dark, but may be less than optimal for visualization under bright lighting conditions, such as when the light source is positioned in front of the volume. In the latter scenario, the pixel values from both images, when summed may overflow/saturate. In some embodiments, as shown in FIG. 7B, a scaling factor may be applied during the summation to address the saturation problem. For example, the final image may be computed by scaling the colorized input 704 by a factor, which is a function of the scalar input M. Here again, optionally user input 711 may be received to control, independent of the summation scaling, the amount of foreground and background information in the final image. Moreover, in some embodiments, the image data may first be normalized within a dynamic range of [0, 1] prior to the summation. In the example in FIG. 7B, a summation function defined by $F=M+(1-M)\cdot I$ may be applied at the fusion block 710' to arrive at the final image 706'. This scaled summation may guarantee that the dynamic range is preserved. As will be appreciated, the scaled summation in the example in FIG. 7B can be seen to inject the background context conditionally to the absence of signal in the foreground, as such reducing the risk of saturation at the output.

Figure 9:
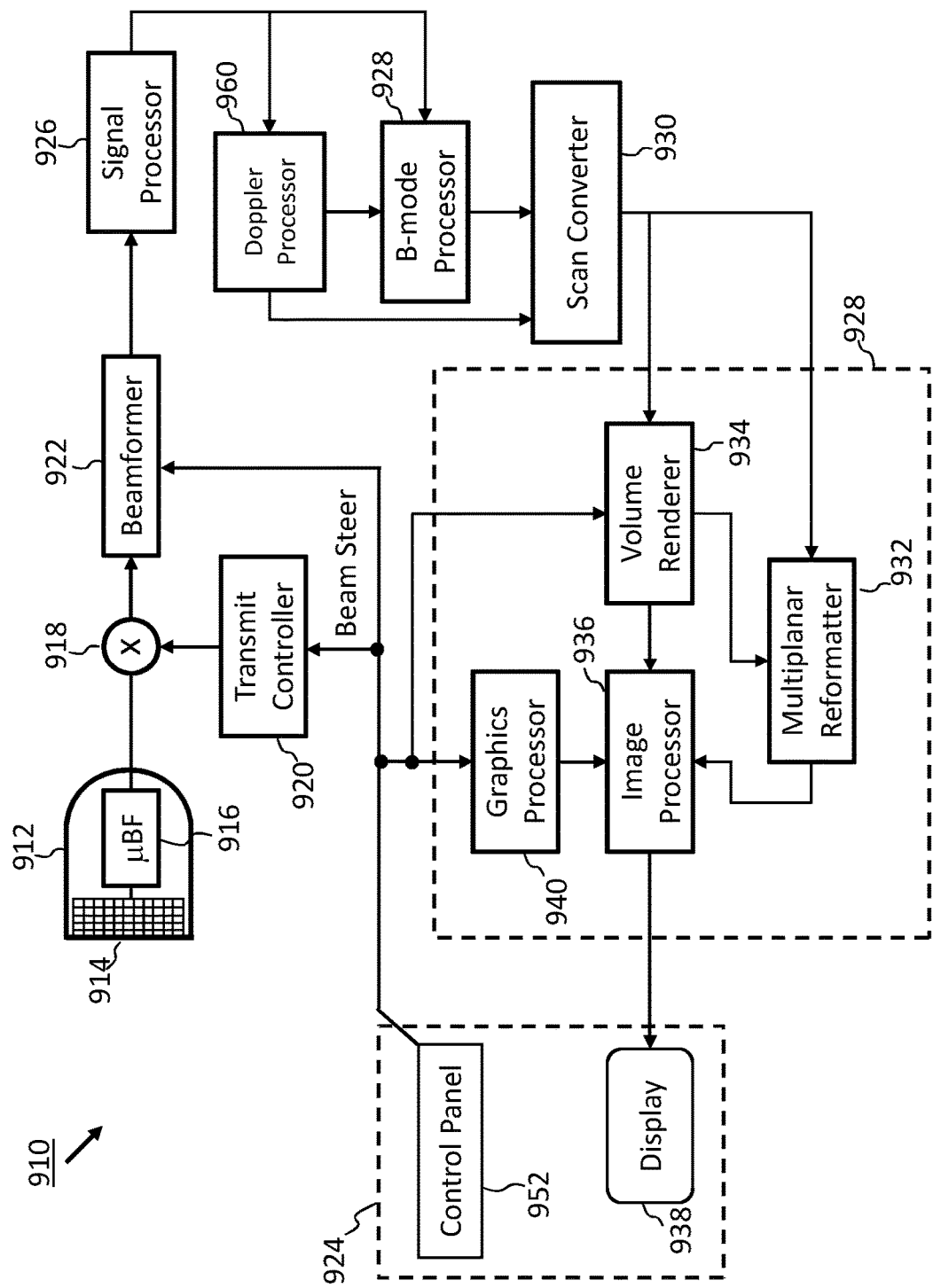
FIG. 9 is a block diagram of an ultrasound imaging system in accordance with some embodiments of the present disclosure.

In some embodiments, a medical image data visualization system in accordance with the principles described herein may be incorporated into an ultrasound scanner or any other type of medical imaging system. FIG. 9 shows a block diagram of an example ultrasound imaging system, which may include a medical image data visualization system according to the present disclosure. The ultrasound imaging system 910 may include at least one processor 928 configured to perform the functions of a processor of a visualization system in accordance with the principles described (e.g., processor 304 of FIG. 3). The system 910 may function as the source of 3D medical image data. That is, the system 910 may be configured, as described further below, to acquire the 3D medical image data and may further be configured to produce composite images, post acquisition or in real-time during the acquisition of the 3D medical image data, for example responsive to invoking an enhanced diagnostic visualization mode of the system.

The ultrasound imaging system 910 may include one or more of the components described above with reference to FIGS. 1-8. Although ultrasound imaging systems are discussed in explanatory examples of embodiments of the invention, embodiments of the invention may be practiced with other medical imaging modalities. Other modalities may include, but are not limited to, magnetic resonance imaging and computed tomography. The techniques described herein may be applied to virtually any imaging modality which can be used to acquire a 3D dataset of medical image data.

The ultrasound imaging system 910 of FIG. 9 includes an ultrasound probe 912 which includes a transducer array 914 for transmitting ultrasonic waves and receiving echo information. A variety of transducer arrays are well known in the art, e.g., linear arrays, convex arrays or phased arrays. The transducer array 914, for example, can include a two dimensional array (as shown) of transducer elements capable of scanning in both elevation and azimuth dimensions for 2D and/or 3D imaging. The transducer array 914 is coupled to a microbeamformer 916 in the ultrasound probe 912. The microbeamformer 916 controls transmission and reception of signals by the transducer elements in the array 914. In this example, the microbeamformer 916 is coupled by the probe cable to a transmit/receive (T/R) switch 918 (although in other examples the two may be wirelessly coupled), which switches between transmission and reception and protects the main beamformer 922 from high energy transmit signals. In some embodiments, for example in portable ultrasound systems, the T/R switch 918 and other elements in the system can be included in the ultrasound probe 912 rather than in a separate ultrasound system base. The transmission of ultrasonic beams from the transducer array 914 under control of the microbeamformer 916 is directed by the transmit controller 920 coupled to the T/R switch 918 and the beamformer 922, which receive input from the user's operation of a user interface 924. The user interface 924 may include a display 938 for displaying image data acquired by the system 910 and one or more user-input devices (e.g., provided on a control panel 952 or on a touch sensitive display).

One of the functions controlled by the transmit controller 920 is the direction in which beams are steered. Beams may be steered straight ahead from (orthogonal to) the transducer array 914, or at different angles for a wider field of view. The partially beamformed signals produced by the microbeamformer 916 are coupled to a main beamformer 922 where partially beamformed signals from individual patches of transducer elements are combined into a fully beamformed signal. The beamformed signals are coupled to a signal processor 926. The signal processor 926 can process the received echo signals in various ways, such as bandpass filtering, decimation, I and Q component separation, and harmonic signal separation. The signal processor 926 may also perform additional signal enhancement such as speckle reduction, signal compounding, and noise elimination. The processed signals are coupled to a B-mode processor 928, which can employ amplitude detection for the imaging of structures in the body. The signals produced by the B-mode processor 928 are coupled to a scan converter 930 and a multiplanar reformatter 932. The scan converter 930 arranges the echo signals in the spatial relationship from which they were received in a desired image format. For instance, the scan converter 930 may arrange the echo signal into a two dimensional (2D) sector-shaped format, or a pyramidal or otherwise shaped three dimensional (3D) format. The multiplanar reformatter 932 can convert echoes which are received from points in a common plane in a volumetric region of the body into an ultrasonic image (e.g., a B-mode image) of that plane, as described in U.S. Pat. No. 6,443,896 (Detmer). The multiplanar reformatter 932 may thus reconstruct a 2D image (an MPR image) from a 3D (volumetric) dataset. The acquired image data may also be coupled to a volume renderer 934, which can convert the echo signals of a 3D dataset into a projected image of the 3D dataset as viewed from a given reference point (also referred to as volume rendering), e.g., as described in U.S. Pat. No. 6,530,885 (Entrekin et al.). The volume renderer 934 may be configured to produce volume renderings and output any other intermediate images, as described herein, for the purpose of producing a composite medical image in accordance with the present disclosure. For example, the volume renderer may be configured to output the images described with reference to FIGS. 5A and 5B.

In some embodiments, the volume renderer 934 may receive input from the user interface 924. The input may include an indication of a selected slice plane, user input for manipulating the volume, e.g., to reposition the volume and/or the light source within the 3D space, or the like. Additionally, the processor 928, which may include or complement the functionality of the volume rendered 934, may also receive inputs to adjust other parameters of the process, for example for setting blending factors, for invoking automatic definition of blending parameters and/or automatic generation of enhanced diagnostic images when in a given visualization (e.g., enhance volume inspection) mode.

In some embodiments, the processor 928 may include an image processor 236 configured to perform enhancements to the images output from the scan converter 230, multiplanar reformatter 232, and/or volume renderer 234. Images produced by the scan converter 230, multiplanar reformatter 232, and/or volume renderer 234 may be coupled to an image processor 236 for further enhancement, buffering, and temporary storage prior to display on the display unit 238. In some embodiments, the image processor 236 may implement one or more of the functions of the processor described herein, e.g., the blending and fusing functions described with reference to FIGS. 6-8. The image processor 236 may be configured to combine B-mode images, Doppler images, or other modality images, with renderings providing depth cues in accordance with the principles described herein. In some embodiments, the processor 928 may include a graphics processor 240 which can generate graphic overlays for display with the images. These graphic overlays can contain, e.g., standard identifying information such as patient name, date and time of the image, imaging parameters, or virtually any type of annotation or marking added to the images, automatically by the system or responsive to user inputs. For these purposes, the graphics processor may receive input from the user interface 224, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit.

Figure 10:
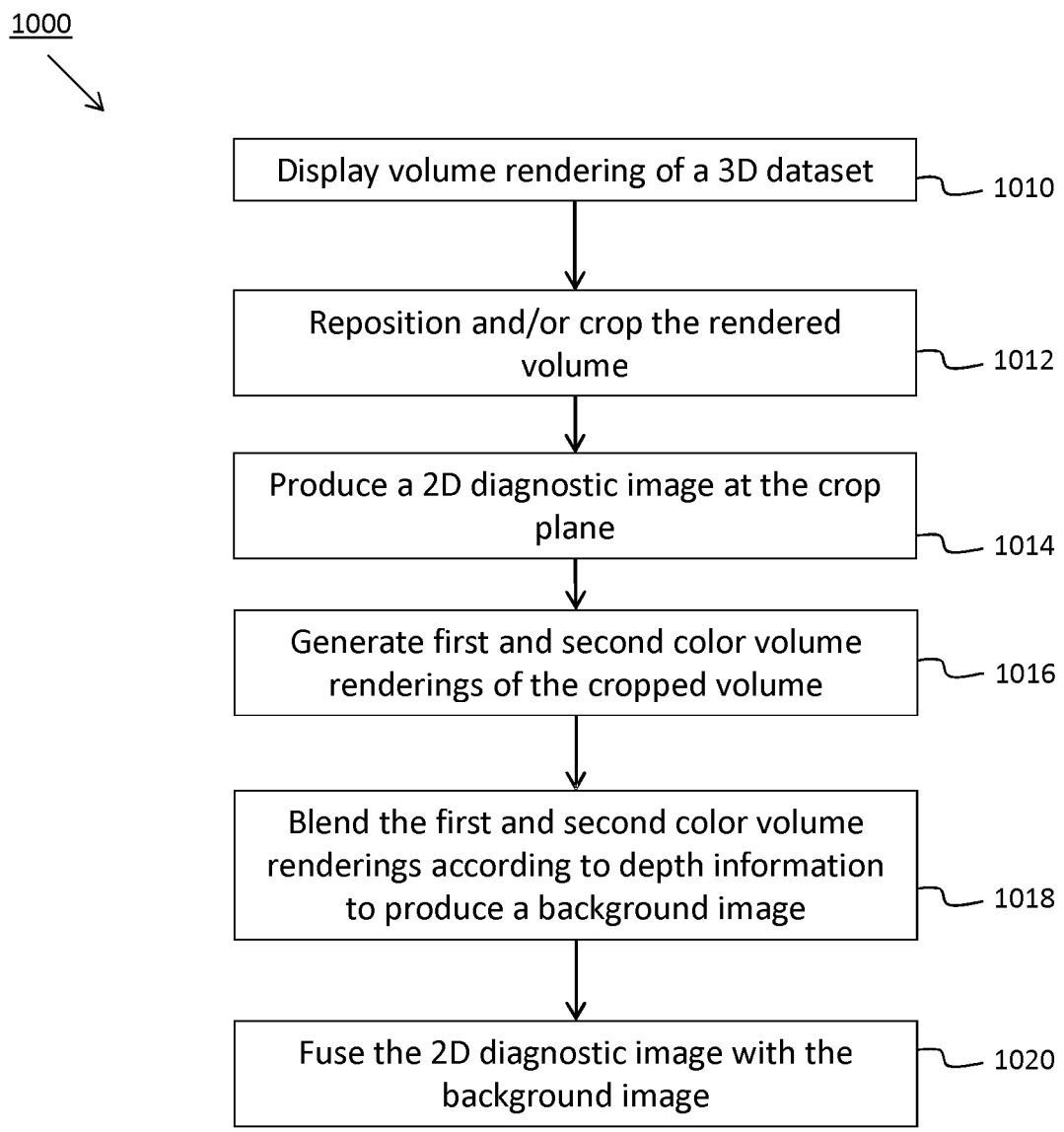
FIG. 10 is a flow diagram of a process in accordance with some embodiments of the present disclosure.

FIG. 10 shows a flow diagram of a method of visualizing 3D medical image data according to some embodiments herein. The method 1000 may include displaying a volume rendering of a 3D dataset representative of a volume of imaged biological tissue (step 1010), cropping the volume responsive to an indication of a selected slice plane (step 1012) and generating a foreground (diagnostic) image comprising a 2D slice image at the selected slice plane (step 1014). The method may further include generating, using a first color map, a first color volume rendering of the cropped volume and generating, using a second color map, a second color volume rendering of the cropped volume (step 1016). The method may further include blending the first and second color volume renderings according to depth information (step 1018) to produce a background image and fusing the foreground image and the background image (step 1020) to produce a composite medical image. The steps of method 1000 and the arrangement thereof shown in FIG. 10 is merely illustrative and any modification such as adding, removing, replacing, or rearranging steps is contemplated. The method 100 may include any of the steps of processes described herein.

For example, in some embodiments, generating the first color volume rendering may include applying a physical model of light propagation through biological tissue to the cropped volume (e.g., to assign hues (or pixel values) for each pixel in the rendering) and encoding the output values from the model in a first multi-channel image. This physical model (or volume-rendering engine) may be implemented according to any known technique (e.g., ray casting, splatting, shear-warping rendering, etc.) to natively produce a colored volume rendering of a 3D dataset. In some such embodiments, generating the second color volume rendering may include producing a single-channel image encoding the estimated depth of structures in the cropped volume, producing a second single-channel image representing a grayscale volume rendering of the cropped volume, and mapping, using a 2D color map, pixel values of the first and second single-channel images to a second multi-channel image that represents the second colored volume rendering. In some embodiments, producing the second single-channel image may include storing one of the multiple channels of the first color volume rendering as the second single-channel image.

In some embodiments, displaying a volume rendering of a 3D dataset representative includes may include positioning the volume in a virtual 3D space in relation to a viewing plane and the method may further include determining a first depth value corresponding to a distance between the viewing plane and a forward most portion of an imaged anatomical structure, determining a second depth value corresponding to a distance between the viewing plane and an aft most portion of the cropped volume, and blending the first and second color volume renderings using a blending function based on the first and second depth values.

In some embodiments, combining the foreground image and the background image may include summing respective pixel values of the foreground and the background image. In some such embodiments, the method may further include applying at least one scaling factor when summing the respective pixel values of the foreground and the background image, wherein one or more of the scaling factors may be derived based on user inputs. In some such embodiments, the method may include receiving user input for adjusting an amount of background and foreground information in the composite medical image and adjusting at least one scaling factor utilized in the combining of the foreground and background images based on the user input.

In some embodiments, the steps of a method according to the present disclosure may be performed by an ultrasound scanner and the method may further include acquiring the 3D dataset of medical imaging data using the ultrasound scanner. Consequently, generating the foreground and background images and combining the image to produce a composite medical image may be performed by one or more processors of the ultrasound scanner. In some embodiments, the 3D dataset may include ultrasound, imaging data and the foreground image may include generating an MPR image at a slice plane through the 3D ultrasound data. In some embodiments, generating the foreground image may include averaging imaging data from a plurality of adjacent imaging planes including the slice plane, e.g., to produce a thick slice 2D image.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. A medical image data visualization system comprising:
an input device connected to a source of 3D medical imaging data;
an output device connectable to a display; and
a processor connected to the input device and the output device and configured to:
receive from the input device a 3D dataset representative of a volume of imaged biological tissue;
crop the volume of the imaged biological tissue at a selected slice plane by removing the portion of the volume between the selected slice plane and a viewing plane;
generate a foreground image comprising a 2D image of bodily structures at the selected slice plane;
generate first and second color volume renderings of the cropped volume of the imaged biological tissue from a same viewing perspective, wherein the first and second color volume renderings are associated with respective first and second different color maps;
blend the first and second color volume renderings to produce a background image; and
combine the foreground image and the background image to produce a composite medical image.

2. The system of claim 1, wherein the processor is configured to produce a first single-channel image and a second single-channel image, and to map, using a 2D color map, pixel values of the first and second single-channel images to a multi-channel image corresponding to the second color volume rendering.

3. The system of claim 2, wherein the processor is configured to estimate, for each pixel in the first single-channel image, a distance between the viewing plane and a first encountered anatomical structure of the cropped volume, and to encode the estimated distances as the respective pixel values.

4. The system of claim 3, wherein the processor is configured to blend pixel values of each pair of corresponding pixels of the first and second color volume renderings as a function of the estimated distance associated with a given pair of pixels.

5. The system of claim 4, wherein the processor is configured to normalize the estimated distances to a range of values between 0 and 1 prior to blending the first and second color volume renderings.

6. The system of claim 1, wherein the processor is configured to determine a depth range with a hybrid technique, wherein the depth range is between a first depth value corresponding to a minimum distance between the viewing plane an imaged anatomical structure and a second depth value corresponding to a maximum distance between the viewing plane and the cropped volume of the imaged biological tissue, and to blend the first and second color volume renderings using a blending function based, at least in part, on the first and second depth values.

7. The system of claim 6, wherein the processor is configured to combine the foreground and background images using pixel-wise summation of corresponding pixel values of the foreground and background images.

8. The system of claim 7, wherein the processor is configured to receive user input for adjusting an amount of background and foreground information in the composite medical image, and to scale the pixel-wise summation based on the user input.

9. The system of claim 1, wherein the input device, the output device, and the processor are components of an ultrasound scanner configured to acquire the 3D dataset.

10. A method of visualizing 3D medical image data, the method comprising:
displaying a volume rendering of a 3D dataset representative of a volume of imaged biological tissue;
cropping the volume of the imaged biological tissue responsive to an indication of a selected slice plane by removing the portion of the volume between the selected slice plane and a viewing plane;
generating a foreground image comprising a 2D slice image at the selected slice plane;
generating a first color volume rendering of the cropped volume of the imaged biological tissue based on a first color map;
generating a second color volume rendering of the cropped volume of the imaged biological tissue based on a second different color map;
blending the first and second color volume renderings to produce a background image, wherein the blending is based at least in part on estimated depth of structures in the cropped volume of the imaged biological tissue; and
combining the foreground image and the background image to produce a composite medical image,
wherein the first and second color volume renderings of the cropped volume of the imaged biological tissue are from a same viewing perspective.

11. The method of claim 10, wherein the generating the first color volume rendering comprises applying a physical model of light propagation through biological tissue to the cropped volume of the imaged biological tissue and encoding output values from the model in a first multi-channel image.

12. The method of claim 11, wherein the generating the second color volume rendering comprises:
producing a single-channel image encoding the estimated depth of structures in the cropped volume of the imaged biological tissue;
producing a second single-channel image representing a grayscale volume rendering of the cropped volume of the imaged biological tissue; and
mapping, using a 2D color map, pixel values of the first and second single-channel images to a second multi-channel image that represents the second color volume rendering.

13. The method of claim 10, wherein the displaying a volume rendering of a 3D dataset representative includes positioning the cropped volume of the imaged biological tissue in a virtual 3D space in relation to the viewing plane, the method further comprising;

determining a depth range with a hybrid technique, wherein the depth range is between a first depth value corresponding to a minimum distance between the viewing plane and an imaged anatomical structure;

determining a second depth value corresponding to a maximum distance between the viewing plane and the cropped volume of the imaged biological tissue; and blending the first and second color volume renderings using a blending function based on the first and second depth values.

14. The method of claim 13, wherein the combining the foreground image and the background image includes summing respective pixel values of the foreground and the background image.

15. The method of claim 14, further comprising applying a scaling factor when summing the respective pixel values of the foreground and the background image.

16. The method of claim 15, further comprising receiving user input for adjusting an amount of background and foreground information in the composite medical image, and adjusting the scaling factor based on the user input.

17. The method of claim 10, further comprising acquiring the 3D dataset of medical imaging data using an ultrasound scanner, and wherein the generating the foreground and background images is performed by one or more processors of the ultrasound scanner.

18. The method of claim 10, wherein the generating the foreground image comprises averaging imaging data from a plurality of adjacent imaging planes including the slice plane.

19. A non-transitory computer-readable medium comprising executable instructions, which when executed cause one or more processors of medical imaging system to perform the method of claim 10.

* * * * *